(12) United States Patent
Yaguchi

(10) Patent No.: US 6,190,039 B1
(45) Date of Patent: Feb. 20, 2001

(54) HEATED TYPE SENSOR WITH AUXILIARY HEATER IN BRIDGE CIRCUIT FOR MAINTAINING CONSTANT SENSOR TEMPERATURE

(75) Inventor: Osamu Yaguchi, Kashiwazaki (JP)

(73) Assignee: Kabushiki Kaisha Riken, Tokyo (JP)

( * ) Notice: Under 35 U.S.C. 154(b), the term of this patent shall be extended for 0 days.

(21) Appl. No.: 09/091,564

(22) PCT Filed: Oct. 22, 1997

(86) PCT No.: PCT/JP97/03813

§ 371 Date: Jun. 22, 1998

§ 102(e) Date: Jun. 22, 1998

(87) PCT Pub. No.: WO98/17994

PCT Pub. Date: Apr. 30, 1998

(30) Foreign Application Priority Data

Oct. 22, 1996 (JP) .................................................. 8-298267
Feb. 27, 1997 (JP) .................................................. 9-060000

(51) Int. Cl.[7] .............................. G01N 27/12; G01K 7/00
(52) U.S. Cl. ............................................. 374/164; 324/725
(58) Field of Search ............................ 324/725; 374/164, 374/165, 173, 163, 172, 183; 219/499, 511

(56) References Cited

U.S. PATENT DOCUMENTS

| | | | | |
|---|---|---|---|---|
| 3,732,432 | * | 5/1973 | Brouneus | 219/499 |
| 3,973,102 | * | 8/1976 | Macklem | 219/511 |
| 4,096,376 | * | 6/1978 | Macklem | 219/511 |

FOREIGN PATENT DOCUMENTS 5-2006 * 8/1993 (JP) ...................................... 374/164

* cited by examiner

Primary Examiner—Diego Gutierrez
Assistant Examiner—Stanley J. Pruchnic, Jr.
(74) Attorney, Agent, or Firm—Hopgood, Calimafde Kalil & Judlowe

(57) ABSTRACT

A main heater, auxiliary heater and guard heater arranged on an insulator substrate to absorb leakage current, thereby maintaining precise sensing temperature. The main heater is parallel with a bridge circuit containing the auxiliary heater, and the main and auxiliary heater s are typically adjacently arranged with a guard heater there between, electrically interconnected to maintain target temperature of the main heater, regardless of leakage current typically resultant from insulation substrate deterioration.

9 Claims, 6 Drawing Sheets

F I G. 4
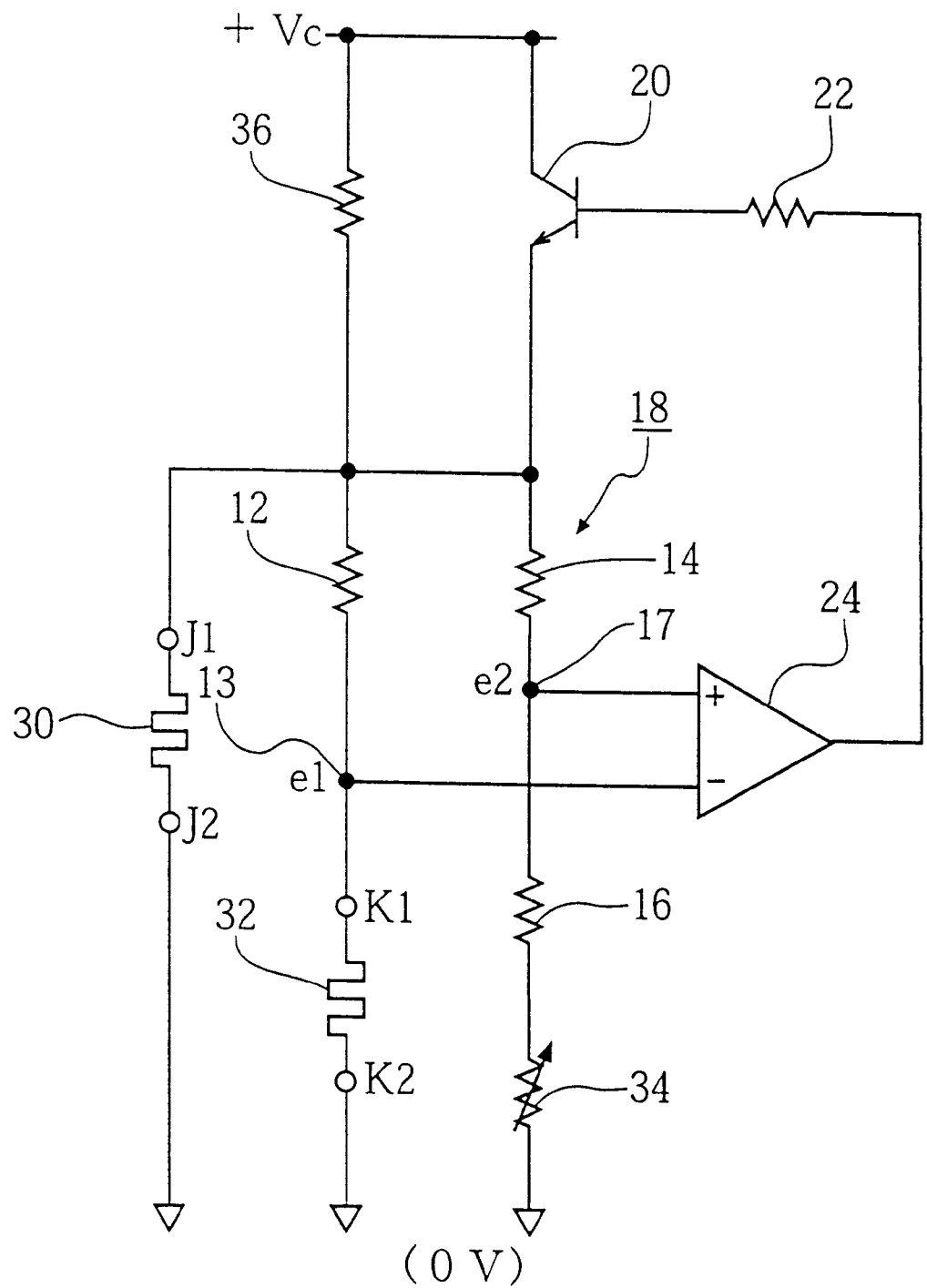

HEATED TYPE SENSOR WITH AUXILIARY HEATER IN BRIDGE CIRCUIT FOR MAINTAINING CONSTANT SENSOR TEMPERATURE

TECHNICAL FIELD

The invention relates to a heated type sensor such as an oxygen or a NOx gas sensor.

BACKGROUND OF THE INVENTION

In a heated type sensor in which a sensing portion of an oxygen or a NOx sensor is heated by a heater, the characteristics of the sensing portion are dependent on its temperature which will vary due to the variation of temperature of the environment or the heater's own temperature variation. A conventional temperature control method for heater in which the heater temperature is maintained to a predetermined value, for example, 300–400° C. is described in the JP-A-60 114,758 official gazette.

The heated type sensor maintains constant temperature of a detective part (3) with a main heater (30) and an auxiliary heater (32). A leakage current originating in the deterioration of the insulation substrate (2) is absorbed by a guard heater.

The good thermal conductivity (high thermal conductivity) insulation substrate or film (2) contains the detective part that is maintained at the high temperature, for example, 400° C., and main and auxiliary heaters are nearly arranged. Alternatively, a guard heater for the leakage current protection is arranged between the main and auxiliary heaters adjacent to the auxiliary heater. A bridge circuit (18) contains the auxiliary heater in one side, and first, second and third resistors (12, 14, 16) in the remaining three sides. The pyro-control circuit comprises an amplifier or a voltage follower (20) which supplies a voltage to the main heater, and another amplifier (24) having an inverting input connected to a serial node between the first resistor and the auxiliary heater, a non-inverting input connected to another serial node between the second and third resistors, and an output end connected to a control input end of the voltage follower. This amplifier controls the power supply voltage to the bridge circuit and the main heater based on the output of the bridge circuit. The second amplifier (52) controls the voltage of a node (50) with the guard heater to be identical to that of the node (13) with the auxiliary heater, based on an output of the second bridge circuit (44) containing auxiliary heater and guard heater (40). (See FIG. 4).

In the aforementioned temperature control method, a thermometric element is disposed adjacent to the heated type sensor with a space therebetween containing gas or ambient air to measure its environmental temperature, and the temperature of the sensing portion is constantly maintained by controlling a power supply to the heater based on the measurement value. The method necessitates the thermometric element by which the temperature of ambient air should be measured, and complex heated type sensor structure and heat control circuitry resulting in higher cost.

Further, an indirect thermal measurement of the sensing portion cannot result in high accuracy because under the condition of gas or air flow through the space, the temperature of the sensing portion is not precisely transferred to the element, and also a delay of temperature transfer to the element can possibly lead to uncontrollable situation such as temperature convergence or divergence.

As another conventional example without any auxiliary heater, a tin oxide film gas sensor is disclosed in 111 page of Nikkei Electronics issued on Jan. 20, 1992 by Nikkei BP publisher. The gas sensor provides four silicon film substrates projected inwardly from a corner of a center-scooped rectangular silicon dioxide substrate chip, and the tin oxide film and platinum heater are deposited on one side of each of the silicon film substrates. The present inventor proposed some improvement regarding the above method in Japanese Patent Application No. 7-328,395.

FIG. 1 shows an example of a well-known bridge type heat control circuit. The circuit comprises a bridge circuit 18 having, for example, a platinum film heater 10 on one side thereof and the resistors 12, 14 and 16 on the remaining three sides thereof, respectively, an emitter follower 20 which supplies a voltage to the bridge circuit 18, and an amplifier 24 having its inverting input connected to a serial node 13 between the resistor 12 and the heater 10, a non-inverting input connected to another serial node 17 between the resistors 14 and 16, and an output connected to the base of the emitter follower 20 through a resistor 22.

Resistance value of the platinum film heater 10 is changed with temperature as the temperature T—resistor R characteristics of FIG. 2. If electric potential values of the serial nodes 13 and 17 are e1 and e2, respectively, the amplifier 24 and the emitter follower connected transistor are so operated that the electric potential e1 is identical to the electric potential e2, i.e., the resistance ratio of the resistor 12 to the heater 10 is identical to that of the resistors 14 to 16 to maintain the temperature of the heater 10 to a predetermined value.

Then, when the temperature of the heater 10 is lower than the predetermined value, output voltage of the amplifier 24 and emitter follower 20 are increased under the condition of e1<e2 to filter increase the power supply to the heater 10. When the temperature of the heater 10 is higher than the predetermined value, output voltage of the amplifier 24 and emitter follower 20 are decreased under the condition of e1>e2 to decrease the power supply to the heater 10.

As described above, it is obvious that the bridge type heat control circuit shown in FIG. 1 has following problems. In order to detect temperature change, i.e., resistance change of the heater 10 precisely, the resistor 12 having higher resistance value than that of the heater 10 may be used. In that case, however, the heat quantity generated in the resistor 12 is also increased more than that in the heater 10. Thus the energy loss by the resistor 12 is increased, the temperature increase of the resistor 12 simultaneously becomes excessive, and then dangerous.

Since the resistance value of the reference resister 12 changes according to its temperature coefficient, it is difficult to obtain an appropriate heater temperature. Moreover, in case that the resister 12 has a positive temperature coefficient of resistance, the temperature and thus the resistance value of the resister 12 are increased when the heater 10 is heated. Therefore, the settling time to e1=e2 is delayed.

BRIEF SUMMARY OF THE INVENTION

Therefore, it is a first object of the present invention to provide a high reliable and low power consumption heated type sensor which is enabled to maintain a predetermined heater temperature by using main and auxiliary heaters even if an environment temperature is changed.

A second object of the present invention is to provide high reliable heaters and those heat control circuits for the heated type sensor in which an leakage current of the main heater does not influence an auxiliary heater even if the electric insulation of the substrate is deteriorated, and thus the main heater can hold a predetermined temperature.

According to the invention, the heated type sensor comprises main and auxiliary heaters arranged adjacent to the sensing portion to heat the sensing portion to a predetermined temperature. These resistance values of the heaters are so determined that a current to the main heater is, for example 10 times, more than that of the auxiliary heater.

In one preferred form of the present invention, the heated type sensor further includes a guard heater arranged on the insulating substrate adjacent to the auxiliary heater between the main and auxiliary heaters. Though the resistance values of the auxiliary and guard heaters are determined higher than that of the main heater, the heater materials are same as that of the main heater. Therefore, these heaters are formed by different mask patterns in case that a predetermined heating element metal is applied or deposited for the same deposition time. Alternatively, the thickness of the main heater may be provided thicker than that of the auxiliary or guard heater by changing deposition time for each heater.

In a heat control circuit, the main heater is connected in parallel to the bridge circuit in which one side is composed of the auxiliary heater and the power is supplied to the bridge circuit and the main heater based on the output of said bridge circuit.

According to the present invention, the heated type contains an insulating substrate on which the sensing portion, the main and auxiliary heaters are adjacently arranged The bridge circuit comprises the auxiliary heater in its one side, and first, second and third resistors in the remaining three sides thereof. The heat control circuit comprises a voltage follower which supplies a voltage to the main heater, and an amplifier having an inverting input connected to a serial node between the first resistor and the auxiliary heater, a non-inverting input connected to another serial node between the second and third resistors, and an output connected to a control input end of the voltage follower.

The insulating substrate has a good thermal conductivity. The sensing portion is formed on its one surface of the insulating substrate and the main heater is formed on the other surface, corresponding to the position of the sensing portion. The auxiliary heater is arranged around the main heater on the other surface of the insulating substrate.

The insulated substrate is a ceramic substrate such as aluminum nitride or silicon carbide whose thermal conductivity is similar to that of metal or silicon dioxide layer for use as a support plate of the sensing portion.

Therefore, the auxiliary heater forms one side of the bridge circuit to mainly detect temperature. The main heater is connected in parallel to the bridge circuit to heat the sensing portion so that an out put of the bridge circuit may be balanced. Because the heat quantity generated in the auxiliary heater is remarkably small compared with that of the main heater, the heat by the first resistor part of FIG. 1 is very small and then a rapid and accurate temperature control becomes possible.

The heat control circuit according to the present invention comprises a main heater connected in parallel to abridge circuit containing an auxiliary heater, a first amplifier controlling a first voltage supplied to the bridge circuit and the main heater, based on the output of the bridge circuit, and a second amplifier controlling a second voltage supplied to the guard heater being identical to a third voltage applied to the auxiliary heater, based on the output of a second bridge circuit containing the auxiliary and said guard heaters.

As for the amplifier, its inverting input is connected to a first node between the first resistor and the auxiliary heater, its non-inverting input is connected to the second node between the second and third resistors, and its output is connected to the main heater and the bridge circuit, for example, through a voltage follower. Power is initially supplied to the bridge circuit by a pull-up resistor.

Alternatively, in the second amplifier, the non-inverting input is connected to the second node, and the inverting input is connected to the guard heater, and the output is connected to the guard heater to supply a current. The second bridge circuit contains the transistor connected to a feeding point between the guard heater and the bridge circuit. A base or gate of the transistor is controlled by the second amplifier to which the voltage of the guard heater is applied.

BRIEF SUMMARY OF THE DRAWINGS

FIG. 4 is a circuit diagram showing an embodiment of the heat control circuit according to the invention.

DETAILED DESCRIPTION OF THE PREFERRED EMBODIMENTS

Embodiments of the invention are described in detail with reference to the drawings.

Figure 2:
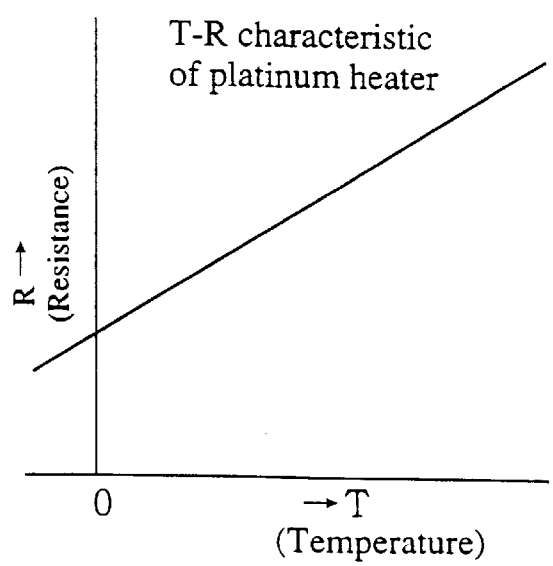
FIG. 2 is a temperature (T)—resistor (R) characteristic of platinum film heater.

Firstly, a heated type sensor of the present invention adds an auxiliary heater to the conventional sensor shown in FIG. 2 of Japanese Patent Application No. 7-328,395. For example, a gas sensing portion is placed between two porous electrode substrates, one being in contact with the gas to be examined, and the other being in contact with the atmosphere. On each porous electrode substrate, a main heater of platinum film or wire is laid, and an auxiliary heater of platinum film or wire is also laid with a space to the main heater.

An electric insulation film with heat resistance and preferable good thermal conductivity is applied on those heaters, and an electrode is further formed on that insulation film. These two porous substrates constructed like this are assembled by facing the electrode as an inside each other. Gas detecting material for example, sintered porous tin oxide or lead oxide, is filled in the inside between two electrodes.

The main and auxiliary heaters are heated to, for example, 410° C., to maintain the entire gas sensor at 400° C. The thinner above electric insulation film is made, the smaller its heat capacity is. Use of the electric insulation film with small heat capacity and good thermal conductivity will make its measurement error small.

Figure 3:
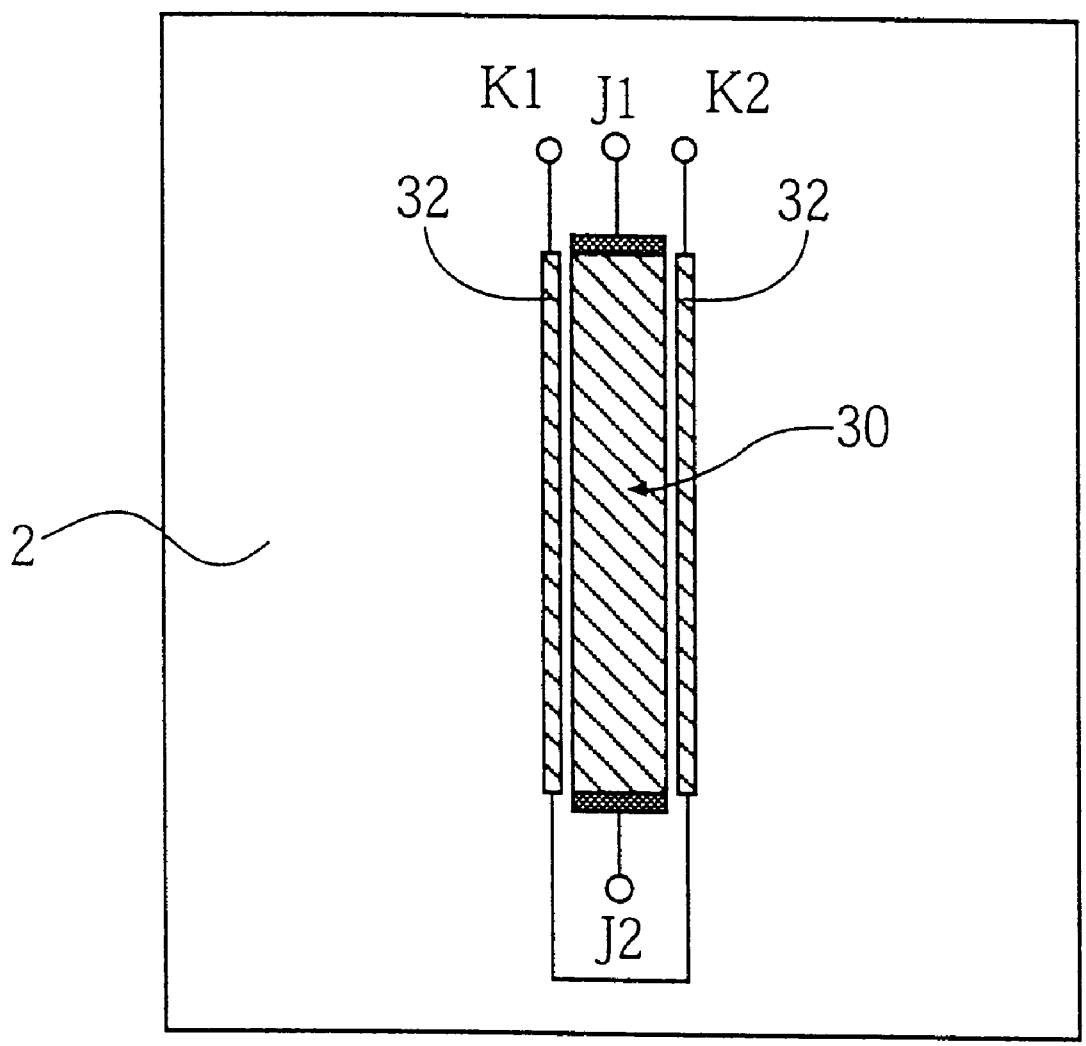
FIG. 3 shows an embodiment of a gas sensor according to the invention and is a schematic plan view in which a sensing portion is arranged on a front side (not shown), and main and auxiliary heaters are arranged on a back side.

In a first embodiment of the heated type sensor as shown in FIG. 3, a gas sensing portion (not shown) to be heated to high temperature is formed on the front side of the insulating substrate 2 with good thermal conductivity and two electrodes (not shown) are formed on its both ends. On the back side of the insulating substrate 2, a main heater 30 of platinum film is formed corresponding to the position of the gas sensing portion so that a heating area may be slightly larger than the gas sensing area. A platinum film auxiliary heater 32 which for example has a target resistance value at 410° C. is arranged around the main heater 30.

In FIG. 3, oblique lines portions show the heating area The main heater 30 and auxiliary heater 32 are preferably made of same material or metal having a same temperature coefficient of resistance, i.e., nickel chromium alloy, platinum or platinum alloy. In this case, temperature change, i.e., resistance change of the main heater 30 is identical to that of the auxiliary heater 32. The main and auxiliary heaters may be platinum films or wires and arranged in meander or concentric circles form.

In order to provide the resistance value of the auxiliary heater higher than that of the main heater using same heater material, these heaters are made using different mask patterns by deposition of a predetermined metal or alloy under the same deposition time, or the thickness of the auxiliary heater may be thinner than that of the main heater by setting the deposition time of the auxiliary heater shorter than that of the main heater.

Figure 1:
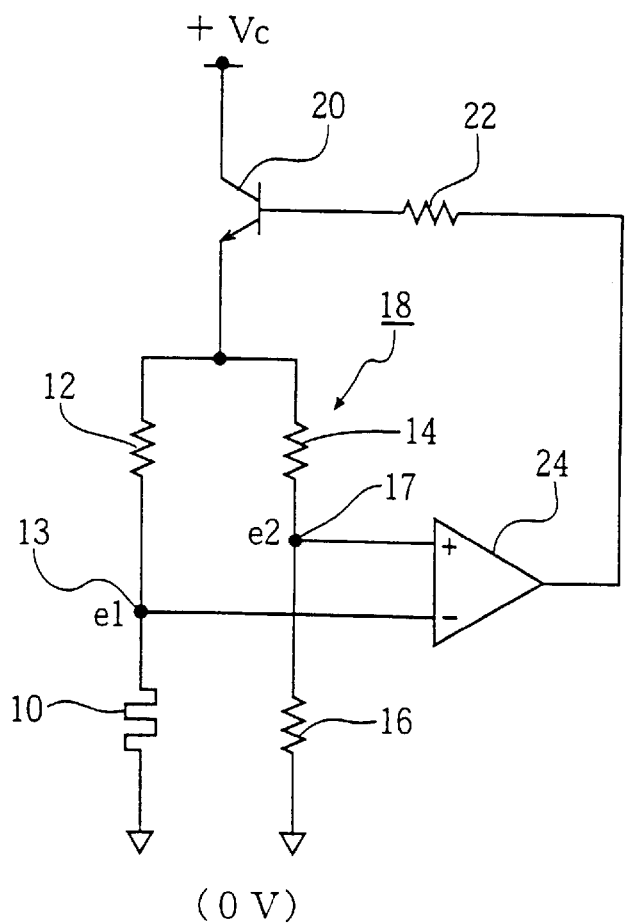
FIG. 1 shows a conventional bridge type heat control circuit.

FIG. 4 is a circuit diagram showing an embodiment of the heat control circuit used for the heated type sensor according to the present invention. In FIG. 4, same numerals are denoted to those similar components shown in FIG. 1. The heat control circuit according to the invention differs from the conventional circuit of FIG. 1 in the following points; the main heater 30 is provided in parallel to a bridge circuit 18, and an auxiliary heater 32 is placed in the position which the conventional heater is placed in the bridge circuit 18. Thus a non-dividable voltage is directly supplied to the main heater 30 in the heat control circuit of the invention.

In other words, in a transistor 20 of the emitter follower connection, a collector is connected to a positive line voltage+Vc line, and an emitter is connected to the bridge circuit 18 and main heater 30. The main heater 30 is grounded. On the other hand, in the bridge circuit 18, a first resistor 12 is connected between the emitter of the transistor 20 and a serial node 13, and the auxiliary heater 32 is connected between the serial node 13 and ground.

Moreover, a second resistor 14 is connected between the emitter of the transistor 20 and a serial node 17, and a third resistor 16 is connected between the serial node 17 and ground through a variable resistor 34. These serial nodes 13 and 17 are respectively connected to inverting and non-inverting inputs of a field effect transistor (FET) or bipolar transistor input-operational amplifier 24, of which input current is negligible. An output of the amplifier 24 is connected to the base of the transistor 20 through a protection resistor 22. Connected between the collector and emitter of the transistor 20 is a pull-up resistor 36 through which an initial voltage is supplied to the bridge circuit 18 in operation when the emitter follower 20 is in an OFF state.

In the basic action of this circuit, because an unbalanced output voltage is not generated in bridge circuit 18 at the initial stage of the power charge, the resistor 36 is necessary to supply an initial voltage, for example, 1 volt to the bridge circuit. A resistance value of this pull-up resistor 36 can be very high because current to the main heater 30 is mainly supplied through the emitter follower 20. Thus power consumption in the resistor 36 can be ignored. Moreover,both main heater 30 and auxiliary heater 32 with positive temperature coefficient of resistance have resistance values that are low at room temperature and gradually increased to reach target resistance values at, for example, 400° C. when current is supplied. Therefore, the bridge circuit 18, amplifier 24 and emitter follower 20 increase the power supply voltage to the main heater 30 and bridge circuit 18 to reach the target voltage by the unbalanced output voltage from the bridge circuit 18 due to the increase in the resistance value of the auxiliary heater 32.

When the temperature of the auxiliary heater 32 is lower than the predetermined value, the output voltage of the amplifier 24 and emitter voltage of the transistor follower 20 are increased under the condition of e1<e2. Thus the power supply to the main heater 30 is increased. When the temperature of the auxiliary heater 32 is higher than the predetermined value, the output voltage of the amplifier 24 is decreased under the condition of e1>e2, and the power supply to the main heater 30 and auxiliary heater 32 is decreased.

Variable resistor 34 is a potentiometer or rheostat which adjusts heater temperature to a desirable value. In the circuit of FIG. 4, a target temperature of the main and auxiliary heaters is provided so that the resistance ratio of the first resistance 12 to the auxiliary heater 32 is set to the value which is identical to that of the second resistor 14 to the sum of third resistor 16 and variable resistor 34.

Therefore, when the temperature of the auxiliary heater 32 is 400° C., the temperature of the main heater 30 is simultaneously regulated to 400° C. according to the power supply. The temperature variation of the main heater 30 influences the temperature of the auxiliary heater 32, and thus the power supply voltage varies in order to make the temperature return to the target value. The target temperature may be set to, for example, 410° C. in consideration of the heat loss by the thermal capacity of the film or substrate placed between the gas sensing portion and heaters.

In the heated type sensor shown in FIG. 3, when the electric insulation characteristics of the substrate on which the main and auxiliary heaters are arranged deteriorate, for example, in aged change, an leakage current is likely to flow between the main and auxiliary heaters. By this leakage current, the electric potential of e1 may be increased, and there may occur a problem that the temperature of the auxiliary heater 32 is lowered from the predetermined value.

Figure 5:
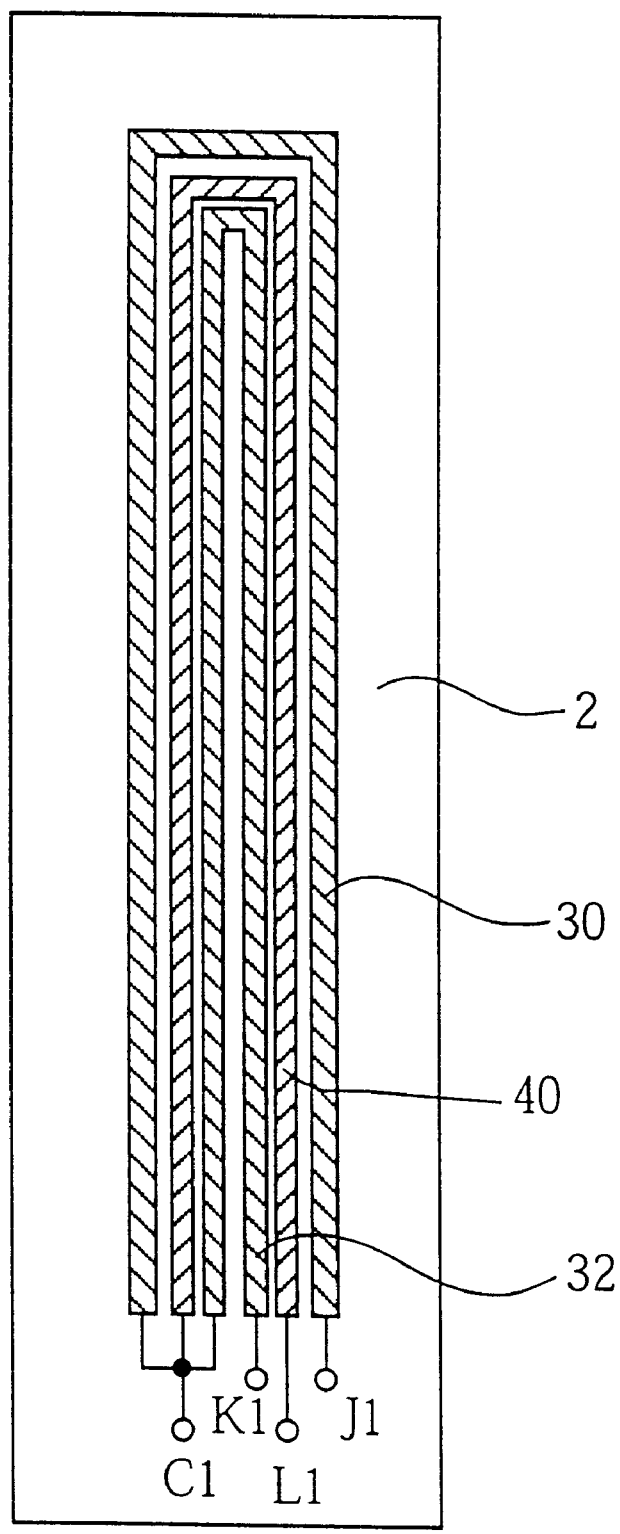
FIG. 5 is a plan view of the heaters for the heated type sensor according to the invention.

FIG. 5 is a plan view showing a second embodiment of the heated type sensor according to the invention to improve the above problem. In FIG. 5, same numerals are denoted to those similar components shown in FIG. 3. The gas sensing portion (not shown) to be heated to high temperature is formed on the front side of zirconia substrate 2 having a good thermal conductivity, and two electrodes (not shown) are formed at its both ends.

On the back side of the substrate 2, a main heater 30 of platinum film is outwardly arranged corresponding to the sensing area. A guard heater 40 of platinum film is surrounded with the main heater 30, and an auxiliary heater 32 of platinum film is surrounded with the guard heater 40. Therefore, the guard heater 40 is arranged between the main heater 30 and the auxiliary heater 32 on the zirconia substrate 2 adjacent to the auxiliary heater 32. If electric potential of each position of the auxiliary heater 32 is identical to that of the guard heater 40 correspondingly adjacent thereto, leakage current from the main heater 30 does not influence the auxiliary heater 32.

Of course, though resistance values of the se auxiliary and guard heaters are provided higher than that of the main heater, heater materials are same as that of the main heater.

Therefore, these heaters are formed by different mask patterns in case that a predetermined heating element metal or alloy is applied or deposited the same deposition time. Alternatively, the thickness of the main heater may be provided thicker than that of the auxiliary or guard heater by changing deposition time for each heater.

Figure 6:
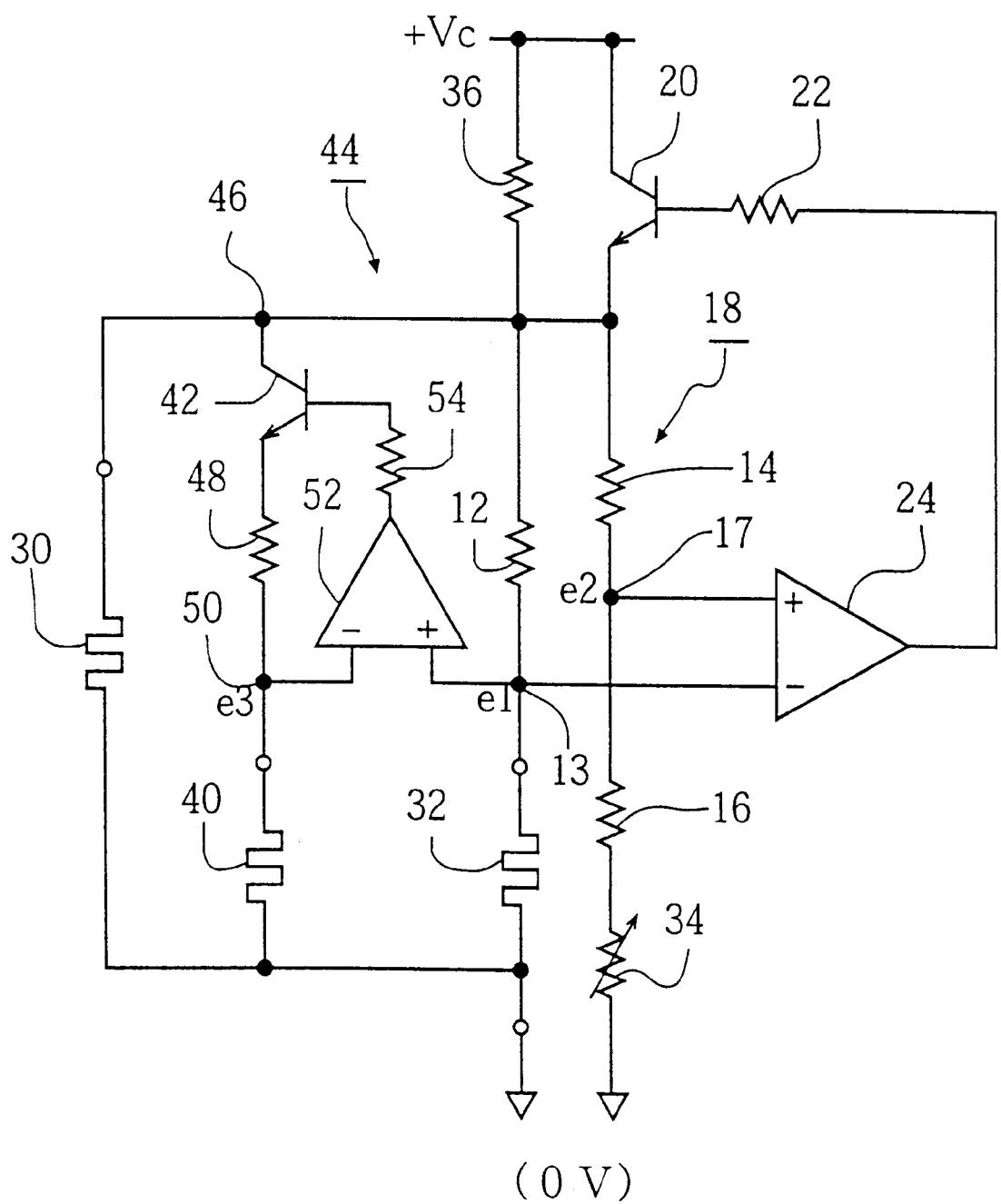
FIG. 6 is a circuit diagram showing a second embodiment of the heat control circuit according to the invention.

FIG. 6 shows a second embodiment of the heat control circuit used for the heated type sensor according to the invention. In FIG. 6, same numerals are denoted to those similar components shown in FIG. 4. In the first transistor 20 having an emitter follower connection, a collector is connected to the positive line voltage+Vc line, and an emitter is grounded through the bridge circuit 18 and main heater 30 which are connected in parallel.

Because the internal resistance of the bridge circuit 18 is much higher than the resistance of the main heater 30, the most of current is supplied to the main heater 30. In this bridge circuit 18, a first resistor 12 is connected in series to the auxiliary heater 32 at anode 13, and a second resistor 14 is connected in series to a third resistor 16 and a variable resistor 34 through a node 17.

These nodes 13 and 17 are connected to the inverting and non-inverting inputs, respectively, of a first operational amplifier 24. An output of the amplifier 24 is connected to the base of the first transistor 20 through a protection resistor 22. A pull-up resistor 36 is connected between collector and emitter of the first transistor 20 in order to supply initial voltage to the bridge circuit 18 for starting.

The first resistor 12 and auxiliary heater 32 compose a second bridge circuit 44 associated with guard heater 40 and second transistor 42. In the second transistor 42, a collector is connected to feeding point 46 of the main heater 30, and an emitter is connected to the guard heater 40 through a resistor 48.

An inverting input of the second operational amplifier 52 is connected to the node 50 between resistor 48 and auxiliary heater 40. In the second operational amplifier 52, a non-inverting input is connected to the node 13, and output is connected to the base of the second transistor 42 through the resistor 54.

Figure 7:
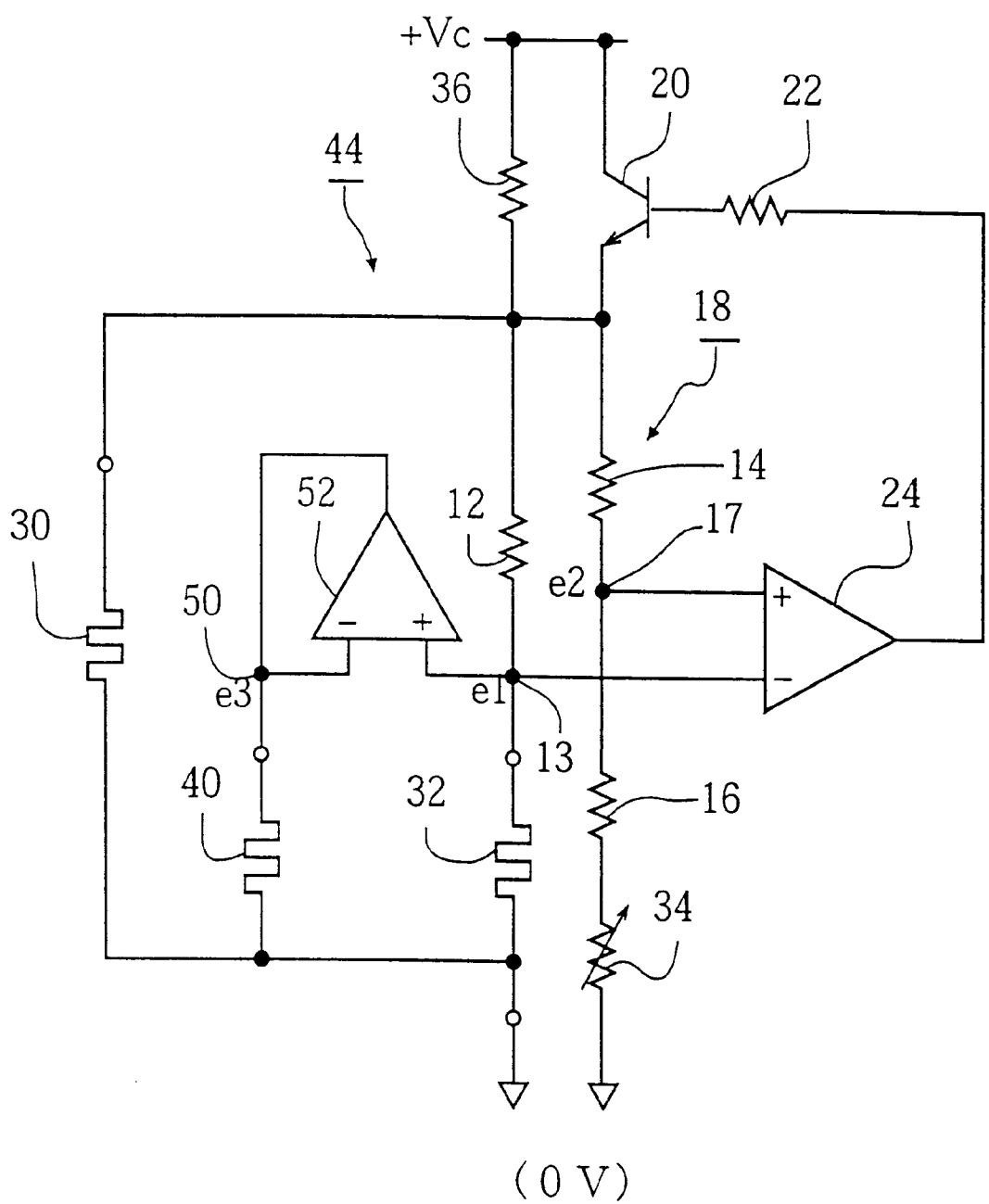
FIG. 7 is another circuit diagram showing a third embodiment of the heat control circuit according to the invention.

FIG. 7 shows a third embodiment of the heat control circuit of the heated type sensor according to the invention. In FIG. 7, same numerals are denoted to those similar components shown in FIG. 6. Because the current supplied to the guard heater 40 is fairly less than that supplied to the main heater 30, the second transistor 42 of the emitter follower connection can be omitted. Therefore, the output of the second amplifier 52 is connected to its inverting input to compose the second bridge circuit 44.

The basic action of heat control circuit according to the second and third embodiments of the invention is as follows. Because unbalanced output voltage is not generated in the bridge circuit 18 at the initial stage of the power charge, for example, an starting voltage of 1 volt is initially supplied to the bridge circuit 18 through a resistor 36. The resistance value of the pull-up resistor 36 can be very high because current to the main heater 30 is mainly supplied tough the emitter follower 20during sensing operation Thus power consumption in the resistor 36 can be ignored.

Moreover, both main heater 30 and auxiliary heater 32 with positive temperature coefficient of resistance have resistance values that are low at room temperature and gradually increase to reach target resistance values at, for example, 400° C. when current is supplied. Therefore, the amplifier 24 and emitter follower 20 increase those power supply voltage, and reach a balanced power supply voltage by an unbalanced output voltage of the bridge circuit 18 due to the increase in the resistance value of the auxiliary heater 32. In other words, the first transistor 20 is controlled by the amplifier 24 so that the electric potential e1 of node 13 is identical to e2 of the node 17 to maintain temperature of the auxiliary heater 32 to the predetermined value.

Therefore, the output of amplifier 24 is increased under e1<e2 when the temperature of the auxiliary heater 32 is lower than the predetermined temperature. Therefore, the voltage supplied to the main heater 30, auxiliary heater 32 and guard heater 40 is increased through the first transistor 20. The output of the amplifier 24 is decreased under e1>e2 when temperature of auxiliary heater 32 is higher than the predetermined temperature. Therefore, the voltage supplied to the main heater 30, auxiliary heater 32 and guard heater 40 is decreased. Of course, almost all current flows through the main heater 30 to mainly radiate heat.

Variable resistor 34 is a potentiometer or rheostat which adjusts the temperature of the auxiliary heater 32 to a desirable value. In the circuit example of FIG. 6 or 7, the auxiliary heater 32 is settled to the temperature defined by R1:rH=R3:(R4+VR1).

Next, the action of the guard heater 40 is describe. Defining the electric potential of the nodes 13 and 50 connected to the auxiliary heater 32 and guard heater 40 are e1and e3, respectively, the output voltage of the second amplifier 52 and the emitter voltage of the second transistor 42 are increased and the electric potential e3 of the guard heater 40 is also increased when e3<e1.

When e3>e1, the output voltage of the second amplifier 52 and the emitter voltage of the second transistor 42 are decreased and e3 is decreased. Therefore, the second transistor 42 is controlled by the second amplifier 52 so that the relation of e3=e1 may be always maintained, and the leakage current influence of the auxiliary heater 32 is avoided.

Even if the leakage current flows from the main heater 30 to the guard heater 40 and electric potential of e3 is increased because the electric insulation characteristic of zirconia substrate 2 is deteriorated, the auxiliary heater 32 is not influenced because e3 becomes equal to e1 at once by the second amplifier 52. In other words, its heater temperature is not varied. The resistor 36 is a pull-up resistor which prevents e1, e2 or e3 from falling to zero electric potential, when the first transistor 20 is turned off In the circuit of FIG. 6 or 7, target temperatures of the main and auxiliary heaters are provided so that the resistance ratio of the first resistor 12 to the auxiliary heater is set to the value which is identical to that of the second resistor 14 to the sum of third resistor 16 plus variable resistor 34). The guard heater 40 has a function that prevents the auxiliary heater 32 from being influenced by the leakage current even if the leakage current caused by the insulation deterioration of the heater substrate flows.

Therefore, when the auxiliary heater 32 is heated up to, for example, 400° C., the target voltage is supplied to the main heater 30, and then the temperature of the main heater 30 simultaneously becomes 400° C. The temperature variation of the main heater 30 influences the temperature of the auxiliary heater 32 and guard heater 40, and thus the power supply voltage varies in order to make temperature return to the target value. The target temperature may be set to, for example, 410° C. in consideration of the heat loss by the thermal capacity of the film or substrate that is positioned between the gas sensing portion and heater The insulating substrate is a ceramic substrate such as aluminum nitride or silicon carbide whose thermal conductivity is similar to that of metal, or silicon dioxide layer for use as a support plate of the sensing portion. Of course MOSFET may be used as the transistor in addition to bipolar type. As described the above, in the heat control circuit of the heated type sensor of the invention, the resistance values of the firs resistor and auxiliary heater can be determined higher than those (the resistance values of the first resistor and main heater) of the conventional bridge type heat control circuit, its ratio can be set to roughly about 1:1 to obtain the maximum sensitivity at predetermined temperature, and its heat quantity generated in the circuit can be extremely reduced. Therefore, the output voltage change (change in e1) due to the resistance or temperature change of the main heater or auxiliary heater can widely range and is capable of more accurate temperature control.

Moreover, in the heat control circuit, its energy loss is decreased and internal temperature rise is also safely limited. Further, because the resistance change of the first resistor served as a reference resistor becomes extremely small, the convergent time to predetermined temperature is shortened as well as accurate temperature control function can be provided.

Therefore, the sensing portion in the ambient air which varies or the heater temperature can be constantly maintained at the high temperature, for example 400° C., and its structure can be simply composed at a low cost as well as its reliability is enhanced. Moreover, since the substrate or film provided between the sensing portion and the heater has a constant thermal conductivity similar to that of metal, and the heat transfer in the substrate is different from the gaseous convection. Therefore, temperature variation of the gas sensing portion or the heater is compensated for its variation, and the sensitivity characteristics of the gas sensing portion become stable.

In the second embodiment of the heated type sensor according to the invention, the second bridge circuit comprises components on the side of the auxiliary heater of the bridge circuit and the guard heater. Because the second amplifier is provided so that the applied voltage (e3) of the guard heater 40 is identical to the applied voltage (e1) of the auxiliary heater 32, even if the electric insulation of the heater substrate such as zirconia is deteriorated, its heater temperature is not varied as the first embodiment of the heated type sensor.

Because the resistance value of the guard heater can be set to large, the output voltage change due to the temperature variation of the main heater can widely range. The temperature rise in the heat control circuit is also restrained.

The auxiliary heater mainly has a temperature sensing function. The main heater is connected in parallel to the bridge circuit to heat the sensing portion so that the bridge circuit may be balanced. Because the guard heater absorbs a leakage current originated from the main heater, a rapid and accurate temperature control becomes possible.

What is claimed is:

1. A heating type sensor in which a main heater and an auxiliary heater are arranged adjacent to a sensing portion to heat said sensing portion to a predetermined temperature, in which said auxiliary heater comprises one side of a bridge circuit; said bridge circuit is parallel to said main heater, a pyro control circuit feeding the power to said bridge circuit and said main heater based on the output of said bridge.

2. The sensor according to claim 1, comprising an insulation substrate on which said sensing portion, said main heater and said auxiliary heater are arranged and in which said bridge circuit contains said auxiliary heater in one side and first, second and third resistors respectively in the remaining three sides, said pyro-control circuit comprises a voltage follower which supplies a voltage to said main heater, and an amplifier having an inverting input connected to the serial node between said first resistor and said auxiliary heater; a non-inverting input connected to the serial node between said second and third resistors and an output connected to a control input end of said voltage follower.

3. The sensor according to claim 2, in which said insulation substrate has a good thermal conductivity, and contains said sensing portion secured on its one surface and said main heater secured on its another surface in alignment with the area of said sensing portion, and said auxiliary heater is arranged around said main heater on said another surface of the insulation substrate.

4. A heating type sensor in which a main heater and an auxiliary heater are arranged adjacent to a sensing portion to heat said sensing portion to a predetermined temperature in which a guard heater is arranged between said main and auxiliary heaters adjacent to said auxiliary heater.

5. The sensor according to claim 4, further comprising:

a main heater paralleled to a first bridge circuit containing an auxiliary heater; a first amplifier controlling a first voltage supplied to said first bridge circuit and said main heater based on the output of the first bridge circuit; and a second amplifier for controlling a second voltage of said guard heater being identical to a third voltage applied on said auxiliary heater based on the output of a second bridge circuit containing said auxiliary and guard heaters.

6. The sensor according to claim 5, in which said first bridge circuit contains first, second and third resistors in the remaining three sides, and said first amplifier having an inverting input connected to a first node between said first resistor and said auxiliary heater, a non-inverting input connected to a second node between said second and third resistors, and an output connected to said main heater and said bridge circuit.

7. The sensor according to claim 5, in which said first bridge circuit comprises at least a first resistor defining a first node between said first resistor and said auxiliary heater and said second amplifier has a non-inverting input connected to said first node, an inverting input connected to said guard heater, and an output connected to supply current to the guard heater.

8. The sensor according to claim 5, in which a transistor is connected to a feeding point between said guard heater and said first bridge circuit, and an output of said second amplifier is connected to the base or gate of said transistor.

9. The sensor according to claim 5, in which said first bridge circuit is initially power supplied by a triggering resistor.

* * * * *